(12) United States Patent
Cartwright

(10) Patent No.: US 6,192,763 B1
(45) Date of Patent: Feb. 27, 2001

(54) METHOD AND APPARATUS FOR DETERMINING THE STRENGTH PATH OF A MORTAR OR CONCRETE MIX

(76) Inventor: Frederick D. Cartwright, 263/15 The Avenue, Heathcote, New South Wales (AU), 2233

( * ) Notice: Subject to any disclaimer, the term of this patent is extended or adjusted under 35 U.S.C. 154(b) by 0 days.

(21) Appl. No.: 09/102,130

(22) Filed: Jun. 22, 1998

(51) Int. Cl.$^7$ ..................................................... G01N 3/00
(52) U.S. Cl. ............................................................. 73/803
(58) Field of Search ........................... 73/790, 784, 786, 73/803, 818, 54.03

(56) References Cited

U.S. PATENT DOCUMENTS

| | | | |
|---|---|---|---|
| 3,631,712 | * | 1/1972 | Mercier ................................ 73/54.03 |
| 4,578,989 | * | 4/1986 | Scott .................................... 73/54.03 |
| 4,703,427 | * | 10/1987 | Catala et al. ........................... 702/12 |
| 4,900,154 | * | 2/1990 | Waitzinger et al. .................... 366/56 |
| 5,396,790 | * | 3/1995 | Koelliker et al. ..................... 73/61.72 |

* cited by examiner

*Primary Examiner*—Max Noori
(74) *Attorney, Agent, or Firm*—Jacobson & Johnson

(57) ABSTRACT

A method of determining the compressive strength path of a mortar or concrete mix is presented. The method includes: (a) conducting a series of tests by directing a jet of gas at gradually increasing pressure onto a surface of a freshly mixed test batch of mortar or concrete mix, monitoring the surface of the test sample and recording the pressure of the gas jet at which erosion resistance of the sample surface breaks down; (b) averaging the recorded gas pressure of the tests to obtain a strength index for the sample, and; © relating the strength index to predetermined set index of mortar or concrete compression strength.

9 Claims, 4 Drawing Sheets

METHOD AND APPARATUS FOR DETERMINING THE STRENGTH PATH OF A MORTAR OR CONCRETE MIX

FIELD OF INVENTION

This invention relates to a method and apparatus for determining the compressive strength pathe of a mortar or concrete mix using the gas jet erosion resistance breakdown of freshly mixed mortar. Strength may be measured in various ways such as compression tensile or shear, compression being the most often specified.

BRIEF DESCRIPTION OF THE PRIOR ART

Basically concrete is a crute material used in volume. Being crude a design strength is set for each type of concrete. Presently however control within this design strength is difficult and this difficulty is covered by an overdesign strength to the lowest reasonable level and in doing so to increase the workability which is of the utmost importance in itself.

Each batch of concrete, made up of its peculiar aggregate, fine aggregate, cement, water and additives assumes its peculiar strength increse path. These peculiar strength paths intertwine as they proceed. It is the control of these peculiar strength paths from variations from their peculiar strength paths thast allows the reduction in over design strength.

The use of this invention would appeal to:
Architects and Engineers who are charged with safety and costs of construction,
Concrete suppliers who would have their production costs reduced and gain business resulting from lower prices and improved quality reliability, and
Structure owners who would gain from improved quality and reduced costs of their structures.

SUMMARY OF THE INVENTION

Accordingly this invention discloses an apparatus for determining the compressive strength path of a concete mix using the gas jet erosion resistance breakdown of freshly mixed mortar, said apparatus comprising a gas nozzle, a frame on which said nozzle is mounted and directed towards the surface of a test batch of said freshly mixed concrete, means on said frame for varying the distance of the nozzle from said surface, means for supplying gas to said nozzle through a range of pressures up to that necessary to effect erosion resistance breakdown of said surfacw and means for indicating the gas pressure supplied to said nozzle.

In another aspect this invention also discloses a method for determining the compressive strength path of a concrete mix, said method including:

A. Conducting a series of tests which comprise
directing a jet of gas at gradually increasing pressure onto the surface of a freshly mixed batch of said concrete.
Monitoring the surface of said concrete and recording the pressure of said gas jet at which erosion resistance of said concrete breaks down.
B. Averaging the recorded gas pressure of said tests to obtain a strength index for said concrete mix, and
C. Comparing said strength index to a predetermined set index of 3, 7, and 28 days compressive concete strength.

BRIEF DESCRIPTION OF THE DRAWINGS

Currently preferred embodiments of the invention will now be described with reference to the attached drawings in which.

DETAILED DESCRIPTION OF THE PREFERRED EMBODIMENT

Figure 1:
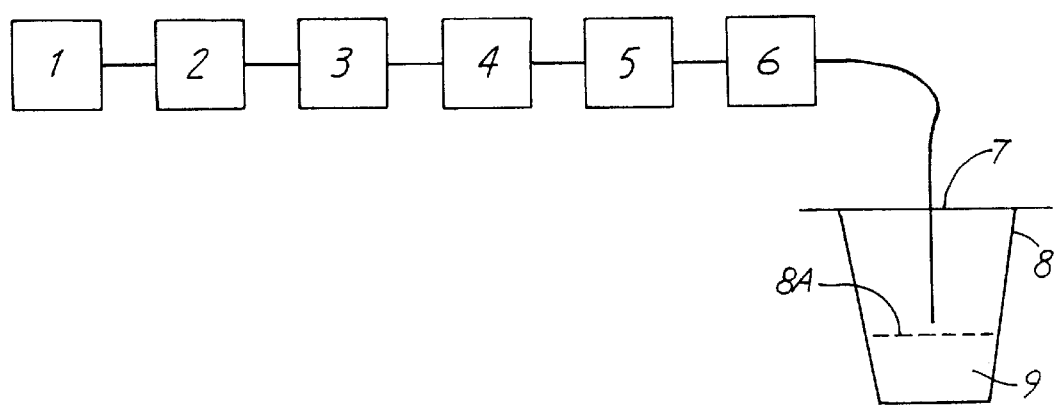
FIG. 1 is a schematic representation of the aforementioned apparatus.

Referring first to FIG. 1 there is a compressior 1, comprssed air receiver 2, control valve 3, water extractor 4, pressure regulating valve 5, preesure guage 6, jet holder 7, test sample container 8 and test sample 9. The jet holder rides on the rim of the test sample container 8 which is parallel to its base which in turn is parallel to the surface 8A of the test sample 9. In this way the jet is directed normally to the test sample surface 8A. The jet is made to slide in the jet holder 7 to enable the jet to be set using a movable spacer to impinge on the surface. Unless stated to the contrary a 12 mm spacer is used.

Test sample container 8 is preferably made of plastic, though any material would be acceptable provided it is not prone to warping nor affecting the Test Sample 9.

Test Sample 9 height in the case of mortar may be say 12 mm and in the case of concretes say 3x the maximum size of the coarse aggregate.

Test Sample Container 8 must have sufficient depth to protect the air jet against surrounding air movement which might affect it.

Figure 2:
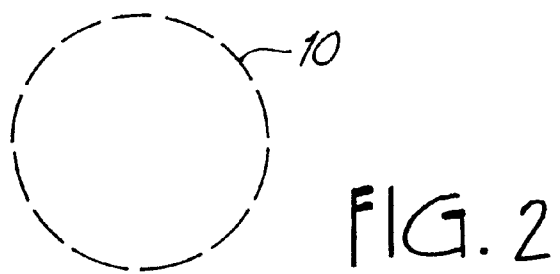
FIGS. 2, 3 and 4 show schematic views of test samples before during and after the erosion breakdown process using the apparatus of FIG. 1.
Figure 3:
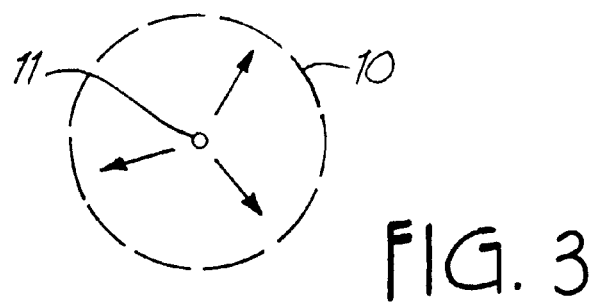
Figure 4:
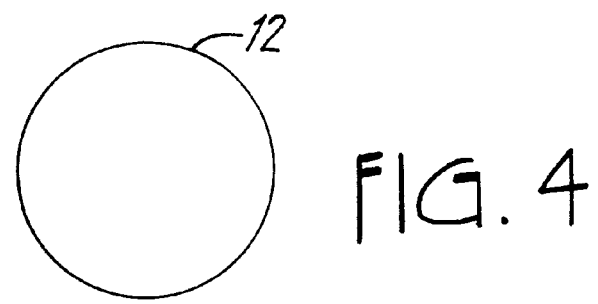

Basiclly the procedure comprises directing a jet of gas onto the mortar surface of freshly mixed concrete, the jet being set at a fixed distance from and preferably normally to the surface after it has been freed from the effects of bleed water. The pressure is gradually increased until the erosion extends over a 15 mm diameter roughly circular area at which point air control valve is closed off and the reading on the pressure gage is recorded. The attached FIG. 2 shows the broken outline of a 15 mm diameter circle 10 encompassing an area free from surface defects and thus suitable for an erosion test, FIG. 3 shows the start of the erosion from the point of impingment 11 of the jet of air and FIG. 4 shows the full outline of the 15 mm diameter circle to which the erosion 12 has reached on closing off of the gas control valve. As will be seen from the adjoined test results produced in accordance with this invention the precision is unequalled by far when compared with any other tests in the mortar and concrete fields.

Experimentation has shown that for a single strength test of freshly mixed correctly apportioned concrete mortar it is necessary to produce an average of ten erosion tests.

Examples of these rare:
a. 55, 35, 40, 45, 42, 55, 40, 35, 50, 45=44.2 kPa average
b. 165, 85, 280, 60, 115, 175, 160, 175, 120, 120=145.5 KPa average This results from the crude nature of concrete and is covered by the design strength. The overall strength results from the inexact operation and is thus additional.

Each average is an index applicable to the concrete strength of its particular mix. If it is for example 10% above the set index the 3, 7 and 28 day strengths will each be 10% above. On the other hand if it is say 10% below the set index then the 3, 7, and 28 days strength will each be 10% lower.

1.0 PROCEDURE FOR SETTING OUT AND EVALUATING EROSION RESISTANCE RESULTS 1.1 By way of example two mortar mixtures were produced from similar materials thus:

| MIXTURE 1 | |
|---|---|
| Moist washed river sand | 1.814 kg (4 lbs) |
| City water | 410 ml |
| Normal portland cement | 0.737 kg (1 lb. 10 ozs) |
| MIXTURE 2 | |
| Moist washed river sand | 0.907 kg (2 lbs) |
| City water | 433 ml |
| Normal portland cement | 1.361 kg (3 lbs) |

The mixtures were hand mixed under ambient atmospheric conditions on different days, the atmospheric temperatures being the same. In the case of each mixture, after completion of the water addition, the relative erosion resistance values, sure guage readings in KPa at material dislodgment, were thus at the times shown.

| | 30 min | 60 min | 90 min | 120 min | 150 min |
|---|---|---|---|---|---|
| | | MIXTURE 1 | | | |
| | 55 | 60 | 70 | 80 | 250 |
| | 35 | 70 | 65 | 100 | 155 |
| | 40 | 50 | 65 | 165 | 190 |
| | 45 | 60 | 110 | 85 | 180 |
| | 42 | 55 | 70 | 110 | 200 |
| | 55 | 50 | 85 | 125 | 205 |
| | 40 | 60 | 90 | 110 | 240 |
| | 35 | 55 | 70 | 75 | 240 |
| | 50 | 45 | 70 | 160 | 210 |
| | 45 | 60 | 60 | 80 | 208 |
| averages | 44.2 | 56.5 | 75.5 | 109.0 | 207.8 |
| | | MIXTURE 2 | | | |
| | 30 min | 60 min | 90 min | 120 min | |
| | 165 | 160 | 235 | 310 | |
| | 85 | 145 | 220 | 320 | |
| | 280 | 175 | 180 | 355 | |
| | 60 | 130 | 230 | 275 | |
| | 115 | 230 | 290 | 360 | |
| | 175 | 235 | 205 | 370 | |
| | 160 | 190 | 290 | 370 | |
| | 175 | 175 | 290 | 375 | |
| | 120 | 215 | 335 | 380 | |
| | 120 | 190 | 250 | 390 | |
| averages | 145.5 | 184.5 | 252.5 | 350.5 | |

1.3 Summing Up 1.31 Hardening progressions are as follows:

| | Mixture 1 | Mixture 2 |
|---|---|---|
| 60 min. average ÷ 30 min. average | 1.28 | 1.27 |
| 90 min. average ÷ 60 min. average | 1.34 | 1.37 |
| 120 min. average ÷ 90 min. average | 1.44 | 1.39 |
| 150 min. average ÷ 120 min. average | 1.91 | not tested |

Thus hardening progressions of similar materials are shown to be reasonably similar.

1.32 Strength relations are as follows:

| | |
|---|---|
| 30 min. average of Mixture 2 ÷ 30 mins. average of Mixture 1 | 3.29 |
| 60 min. average of Mixture 2 ÷ 60 mins. average of Mixture 1 | 3.27 |
| 90 min. average of Mixture 2 ÷ 30 mins. average of Mixture 1 | 3.34 |
| 120 min. average of Mixture 2 ÷ 120 mins. average of Mixture 1 | 3.22 |
| Average | 3.28 |
| Variation ± | 1.83% |

Thus strength relations of similar materials are shown to be reasonably consistent.

Figure 5:
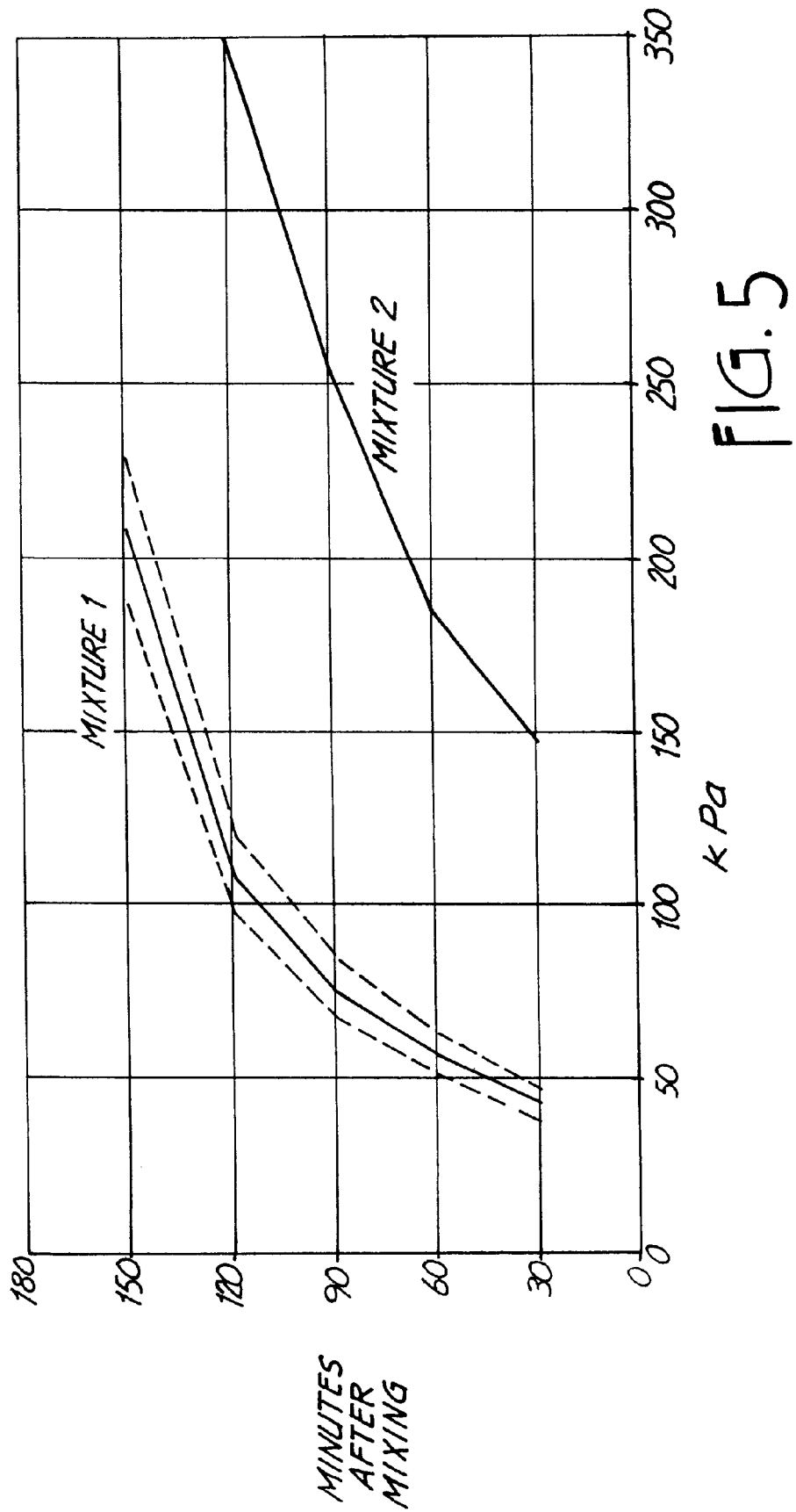
FIGS. 5 and 6 show graphical respresentations of the test sample results.

1.4 FIG. 5 shows graphical representations of the mixture average erosion resistance values at their times of determination.

1.41 These are usually peculiar to the basic materials of their make up.

Figure 6:
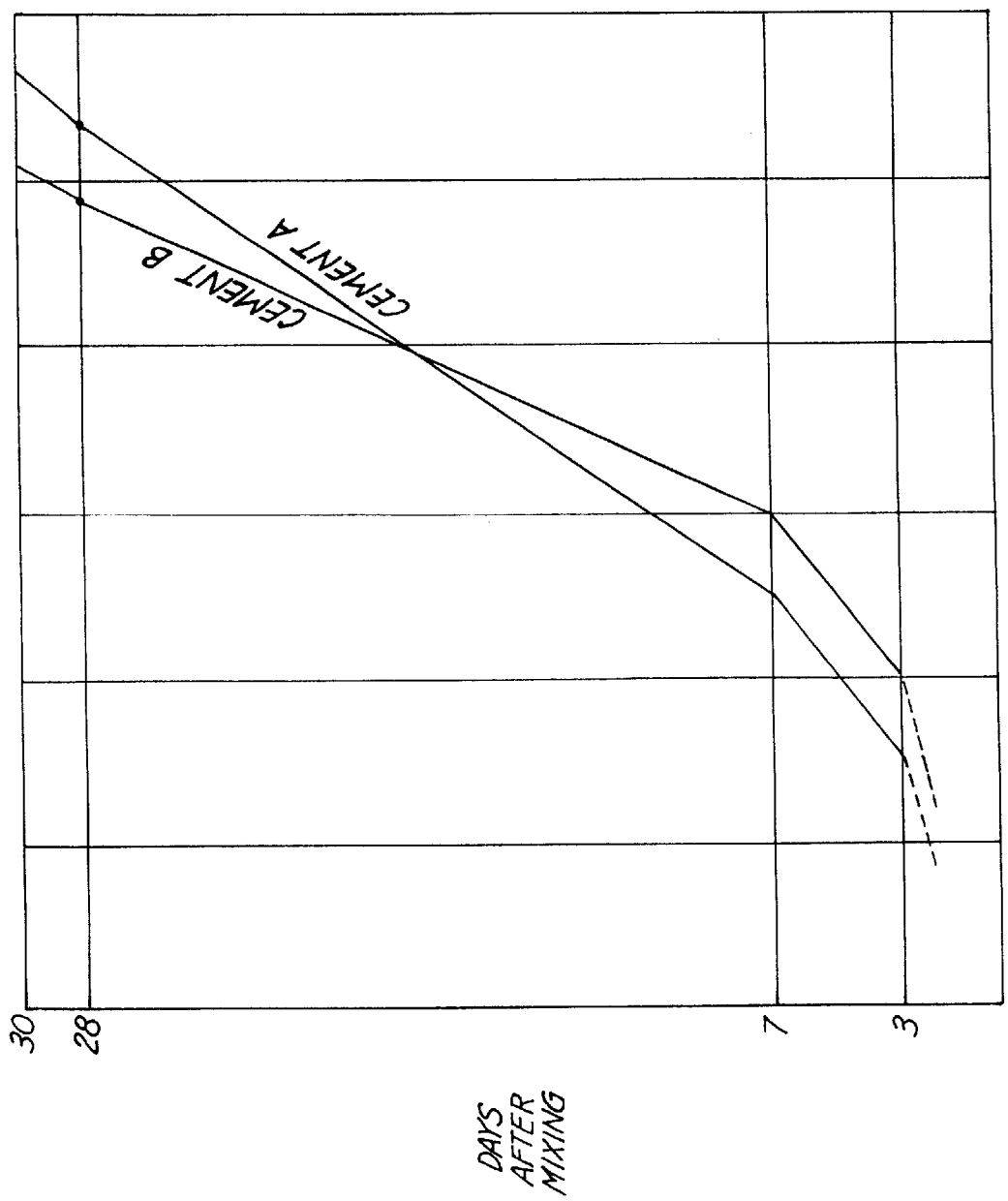

Drawing on general knowledge in support of this, FIG. 6 shows the differences and thus the peculiar natures of the hardening progressions of two cements of the same type at the same water: cement ratio in concrete. Cement B has higher 3 days and 7 days strengths than Cement A while Cement A has a higher 28 day strength than Cement B.

2.0 Having established the relation between the erosion resistance break down of the mortar of a concrete mixture on completion of mixing and the compressive strength of the same concrete at a later time, usually 28 days, the erosion resistance break down of the mortar of a succeeding concrete mixture made from similar materials can be used as a rapid means of determining whether or not the compressive strengths at the later time will be as required.

2.1 For example in FIG. 5 the dotted line to the right of the Mixture 1 solid line indicates a 10% increase in compressive strength each time—pressure being increased by 10%. Likewise the dotted line to the left of the Mixture 1 solid line indicates a 10% decrease in compressive strength each time—pressure being decreased by 10%.

2.2 Should the erosion resistance graphical representations of succeeding concrete mixtures made from presumed similar materials not conform to the basic graphical representation as determined for the specific mixture the operation is out of control and requires attention.

3.0 For each peculiar mix and thus for its peculiar strength path to pass through the desired compressive strengths, a graph must be produced under laboratory conditions starting from the freshly mixed strength and based on the water/cement value. For this dry aggregate must be used. As indicated in Item 1 for each similar peculiar mix, depending on whether the freshly mixed strength is higher or lower the water/cement ratio may be raised or lowered to keep the production in reasonable compressive strength balance.

3.1 Laboratory tests are usually performed at 22C whereas field tests take place over a wider temperature range. Thus for each peculiar mix its freshly mixed strength must be determined by the laboratory at say 32C, 27C, 17C and 12C and a graph provided. Lower temperature strengths will be lower than high temperature strengths and the graph will allow field operators to make the necessary temperature strength adjustments.

4.0 FIELD MIXING AND DESPATCH FACILITY

Coarse and fine aggregates are stored in the open according to size, type and source, and may thus contain moisture. Cement and additives are stored under dry conditions according to the type and source. Water is sourced from the local potable supplies.

5.0 Laboratory tests must be made from seperate samples sent from the field mixing and despatch facility prior to initial start-up of the facility production and as often thereafter as considered necessary. Materials must continue to be obtained from those sources to which laboratory test information refers. In the event of its being necessary to make a material change new laboratory test information must first be obtained and all relevant compartments cleaned out before introducing the new material. A freshly mixed strength must be determined by the facility on initial start-up for each mix to take into account moisture conditions in the materials stored in the open, and as often thereafter as found necessary. Continuously sourced materials may change as time goes on and this makes it necessary for the facility, if its tests appear to show that this may be happening to have the relevant laboratory tests repeated.

6.0 POSITIONS OF DISCHARGE

Freshly mixed strengths my be retaken at points of discharge from the information available and should there be anything untoward appropriate action can be taken.

7.0 From the forgoing it has been shown that each specific (peculiar) mix can have its own strength pedigree starting from the as mixed strengths at say 5 minutes, 10 minutes, 15 minutes, 30 minutes, 60 minutes, 90 minutes and 120 minutes after mixing and proceeding upwards through say 3 days, 7 days, 14 days, 21 days and onwards. Thus the ability to determine as mixed strengths in accordance with this invention is the key to the strength control of concrete structures. If the strength index of a mix is taken at say 30 minutes after mixing the workability limit might be set at say 60 minutes, 90 minutes, 120 minutes or 150 minutes after mixing.

8.0 A PROCEDURE TO PREPARE A CONCRETE TEST SAMPLE FOR TESTING a. Use a plastic container prefrerably circular with a turned over rim. In the making of the moulds in which there are made the base and the rim are parallel.

b. Use a flat level surface onto which to drop the container when loaded with test material. The height of drop say 2 centimeters and the number of drop times may be varied to suit the material to be tested. This will bring sufficient mortar above the coarse aggregate to allow testing without unduly striking the coarse aggregate and will produce a certain amount of compaction. Before commencing the dropping action and at suitable times during the dropping action while the container is on the flat surface jerk the container to left and to right to assist in the action.

c. After obtaining a suitable surface of mortar for testing allow the container to rest on the flat level surface until it's time for testing when it is placed in its position at the test instrument, which position is slightly canted towards the operator to allow the bleed water to remain in the lower part of the test area and thus permit testing in the upper part. In the event of striking an occasional piece of coarse aggregate discard the reading and make a replacement test for that reading.

OPERATIONAL ANNEX

1. Where strengths, be they compressive, tensile, shear or whatever, at say 3 days, 7 days, 14 days, 21 days, 28 days and onwards are determined by conventional means and these require consideration of a number of test pieces the same number of test pieces should be considered in the determining of the relative strength indices of the freshly mixed mortar or concretes.

2. THE SELECTION OF A MATERIAL FOR THE PURPOSES OF PROVING THE PROCEDURE AND THE TRAINING OF OPERATING TECHNICIANS.

Packaged, Dry, Combined Materials for Mortar and Concrete have been selected for the following reasons:

a. They are covered by ASTM Specification C387 which requires a minimum compressive strength of 24.1 MPa at 28 days for the average of 3 test specimens none of which shall have a compressive strength less than 90% of the average.

b. They are means for tying strength indices envisaged in this patent application to compressive strengths.

c. They are commercially available at low cost.

d. They are appropriate for the initial training of operating technicians and for refresher purposes.

"Concrete Mix" manufactured by Handy Mix Mfg. Co. Pty. Ltd. of No. 1 Tennyson St. Granville, NSW meets the requirements and has been selected for use the minimum compressive strength being claimed to be 25 MPa at 28 days.

3. Proving Test Results

Atmospheric temperature range 20–22° C.

Material weight per test=2.93 kg=6.47 lbs

--- a) 330 ml water additions to obtain 25 MPa a) tests made 30 minutes after water addition
    b) tests made 60 minutes after water addition Test 1 a) 45, 65, 62, 48, 48, 45, 45, 52, 38, 52 average     50.0
        b) 62, 82, 75, 55, 78, 71, 80, 78, 54, 53 average            68.8
Test 2 a) 54, 49, 45, 50, 42, 48, 61, 51, 61, 45 average     50.6
        b) 68, 63, 77, 61, 92, 52, 60, 57, 52, 70 average            65.2
Test 3 a) 53, 53, 55, 49, 52, 36, 51, 37, 44, 65 average     49.5 b) 77, 72, 61, 65, 56, 49, 66, 67, 54, 72 average            63.9

Totals 150.1
                                       Totals         197.9
                         Average of totals   50.0    66.0

$$\frac{\text{Lowest strength}}{\text{Average strength}} \times 100 \text{ at } a)\frac{49.5}{50.0} \times 100 = 99.0\%$$

$$b)\frac{63.9}{66.0} \times 100 = 96.8\%$$

b) 400 ml water additions to obtain less than 25 MPa.

i.e. $25 \times \frac{330}{400} = 20.625$ MPa a) tests made 30 minutes after water addition
    b) tests made 60 minutes after water addition Test 1 a) 48, 38, 45, 54, 41, 40, 38, 34, 40, 38 average     41.6
        b) 67, 60, 40, 42, 57, 42, 43, 50, 50, 58 average            50.9
Test 2 a) 40, 45, 39, 43, 45, 43, 35, 41, 42, 35 average     40.8
        b) 54, 53, 56, 55, 55, 57, 58, 47, 63, 58 average            55.6
Test 3 a) 50, 42, 40, 55, 40, 45, 35, 35, 36, 40 average     41.8 b) 47, 62, 51, 47, 40, 65, 40, 60, 50, 53 average            51.5

Totals 124.2
                                     Totals         158.0
                         Average of totals   41.4
                                                                52.7

$$\frac{\text{Lowest strength}}{\text{Average strength}} \times 100 \text{ at } a)\frac{40.8}{41.4} \times 100 = 98.6\%$$

$$b)\frac{50.9}{52.7} \times 100 = 96.6\%$$

The foregoing meet the strength requirements of ASTM C387. Consideration of Strengths Vis-a-Vis Water Cement Ratios $$\frac{\text{300 ml water content}}{\text{400 ml water content}} \quad a) 50 \times \frac{330}{400} = 41.25$$

$$b) 66 \times \frac{330}{400} = 54.45$$

thus variations from actual tests are a) $\frac{0.15}{41.40} \times 100 = 0.36\%$ below b) $\frac{1.75}{52.70} \times 100 = 3.32\%$ above Consideration Of Strengths Vis-A-Vis Time The ten individual tests the average of which make up a test should be made within 5 minutes. During this period the mortar is gradually gaining strength. Thus if a second set of ten individual tests is made in the following five minutes their average should show an increase in the vicinity of 5/30 or 1/6 of the difference between the tests at a) and b). To demonstrate this a test was made after that shown under 400 Ml water addition Test 3b) with the following results:

45, 52, 54, 62, 52, 51, 48, 64, 47, 55 53.0 average

Test at 3b)–test at 3a)=51.5–41.8=9.7

1/6 of 9.7 =1.62

Therefore 51.5+1.62=53.12

4 CONSIDERATION OF CLAUSE 5, 2ND PARAGRAPH

When rain falls on the aggregates stored in the open it drains downwards fairly evenly in the case of coarse aggregate. This is not so in the case of fine aggregate and water retention builds up on its way to the bottom of the pile. For this reason it is necessary to determine the water contents at appropriate intervals. An easy way of doing this would be the use of a standard cement mixed with appropriate quantities of the dry aggregates and water for which a strength index is determined. Thereafter a strength index of a later test will indicate the water content of the aggregates.

5. The proving Test Results shown in 3 above were made with a spacing of 12 mm between the jet and the test material. In order to increase the KPa numbers of the air jet to make them more meaningful when dealing with low strength material such as 5 MPa concrete the spacing between jet and test material was doubled with the following results:

Material—'Concrete Mix' (2.93 kg—6.47 lbs—Water addition—330 mls)

MPa—25 at 28 days

Temperature=21° C.

Spacing—24 mm between jet and test material, i.e. 2×previous spacing

Time—30 minutes after mixing (water addition)
140, 100, 80, 83, 97, 140, 92, 130, 142, 150, average= 115.4
   60 minutes after mixing (water addition) 180, 140, 138, 130, 124, 225, 160, 150, 160, 110, average 151.7

It will thus be appreciated that this invention at least in the form of the embodiment disclosed provides a novel and useful procedure for determining the strength path of a mortar or concrete mix using the gas jet erosion resistance breakdown of freshly mixed mortar. Clearly however the examples described are only the currently preferred forms of this invention and a wide variety of modifications may be made which would be apparent to a person skilled in the art. For example the design of the various components shown in FIGS. 1 to 3 may be changed according to application. The invention is also not limited to any particular sensing device for detecting and amplifying the gas jet rupture noise of the mortar surface, The claims defining the invention are as follows:

1. A method of determining the compressive strength path of a mortar or concrete mix, containing coarse aggregate said method comprising the steps of:
   (a) conducting a series of tests which each comprise:
      directing a jet of gas at gradually increasing pressure onto a surface of a freshly mixed test sample of said mortar or concrete mix,
      monitoring the surface of said test sample and recording the pressure of said gas at which erosion resistance of said surface breaks down,
   (b) averaging the recorded gas pressures of said tests to obtain a strength index for said mortar or concrete mix, and
   (c) relating said strength index to a predetermined set index of mortar or concrete compressive strength.

2. The method as claimed in claim 1 wherein said series of tests are conducted at about 5, 10, 15, 30, 60, 90, 120 and 150 minutes after mixing of said concrete or mortar.

3. The method as claimed in claim 2 wherein said predetermined set index of compressive strength is for 3, 7, 14, 21 and 28 days and onwards after mixing.

4. The method as claimed in claim 3 wherein the gas jet is directed normally to the test sample surface.

5. The method as claimed in claim 4 wherein before conducting said series of tests a test sample of said mortar or concrete mix is deposited in a test sample container and said mortar or concrete mix and sample container are subjected to a dropping action to produce a level test area and in the case of the concrete mix a layer of mortar above the coarse aggregate as well.

6. The method as claimed in claim 5 wherein during said dropping action the test sample container is jerked from side to side to assist the dropping action.

7. The method as claimed in claim 6 wherein said test sample container is canted to one side during said series of tests so as to allow bleed water to collect on the lower part of the sample surface and allow testing on the upper part thereof.

8. Apparatus for determining the compressive strength path of a mortar or concrete mix using the method as claimed in claim 1, said apparatus comprising a gas nozzle, a frame means on which said nozzle is mounted and directed towards the surface of said test sample, means on said frame for varying the distance of the nozzle from said surface, means for supplying gas to said nozzle through a range of pressures up to that pressure necessary to effect erosion resistance breakdown of said test sample surface and means for indicating and recording the gas pressure supplier to said nozzle.

9. The apparatus as claimed in claim 8 wherein said frame is adapted to allow said jet to be set at a chosen one of a range of distances from said test sample surface.

* * * * *